US011688106B2

(12) United States Patent
Hewitt et al.

(10) Patent No.: US 11,688,106 B2
(45) Date of Patent: Jun. 27, 2023

(54) GRAPHICAL ADJUSTMENT RECOMMENDATIONS FOR VOCALIZATION

(71) Applicant: International Business Machines Corporation, Armonk, NY (US)

(72) Inventors: Trudy L. Hewitt, Cary, NC (US); Christian Compton, Austin, TX (US); Merrilee Freeburg Tomlinson, Cary, NC (US); Christina Lynn Wetli, Raleigh, NC (US); Jeremy R. Fox, Georgetown, TX (US)

(73) Assignee: International Business Machines Corporation, Armonk, NY (US)

( * ) Notice: Subject to any disclaimer, the term of this patent is extended or adjusted under 35 U.S.C. 154(b) by 123 days.

(21) Appl. No.: 17/216,055

(22) Filed: Mar. 29, 2021

(65) Prior Publication Data

US 2022/0309716 A1 Sep. 29, 2022

(51) Int. Cl.
*G09G 5/00* (2006.01)
*G06T 11/00* (2006.01)
(Continued)

(52) U.S. Cl.
CPC ............... *G06T 11/00* (2013.01); *G06T 7/50* (2017.01); *G06T 7/70* (2017.01); *G06V 20/20* (2022.01);
(Continued)

(58) Field of Classification Search
CPC ....... G06T 19/006; G06T 19/00; G06F 3/011; G06F 3/012; G02B 27/017
(Continued)

(56) References Cited

U.S. PATENT DOCUMENTS 8,918,162 B2 12/2014 Prokoski
10,522,052 B2 12/2019 Al-Harbi
(Continued)

FOREIGN PATENT DOCUMENTS

CN 107077201 A 8/2017
CN 109147825 A 1/2019
(Continued)

OTHER PUBLICATIONS

Ali et al., "Lip Syncing Method for Realistic Expressive 3D Face Model," Multimedia Tools and Applications, vol. 77, Issue 5, Mar. 2018, 59 pages.

(Continued)

*Primary Examiner* — Gordon G Liu
(74) *Attorney, Agent, or Firm* — Eric W. Chesley (57) ABSTRACT

Audio of a user speaking is gathered while spatial data of the face of the user is gathered. Positions of elements of the face of are identified, wherein relative positions of the elements cause a plurality of qualities of the user voice. A subset of positions of the elements are identified to have caused a detected first quality of the user voice during the period of time. Alternate positions of the one or more elements are identified that are determined to cause the user voice to have a second quality rather than the first quality. A graphical representation of the face that depicts one or more adjustments from the subset of the positions to the alternate positions is provided to the user.

20 Claims, 5 Drawing Sheets

(51) Int. Cl.
| | |
|---|---|
| *G10L 15/00* | (2013.01) |
| *G06T 7/70* | (2017.01) |
| *G10L 15/22* | (2006.01) |
| *G06T 7/50* | (2017.01) |
| *G06V 20/20* | (2022.01) |
| *G06V 40/16* | (2022.01) |
| *A61B 5/00* | (2006.01) |
| *G09B 19/04* | (2006.01) |

(52) U.S. Cl.
CPC .......... *G06V 40/171* (2022.01); *G10L 15/005* (2013.01); *G10L 15/22* (2013.01); *A61B 5/0077* (2013.01); *G06T 2207/30201* (2013.01); *G06V 40/178* (2022.01); *G09B 19/04* (2013.01)

(58) Field of Classification Search
USPC ........................................................ 345/633
See application file for complete search history.

(56) References Cited

U.S. PATENT DOCUMENTS

| | | | |
|---|---|---|---|
| 10,586,368 B2 | 3/2020 | Cao | |
| 10,699,705 B2 | 6/2020 | Li | |
| 10,755,463 B1 | 8/2020 | Albuz | |
| 10,806,393 B2 | 10/2020 | Einfalt | |
| 10,885,317 B2 | 1/2021 | Yoo | |
| 2006/0009978 A1 | 1/2006 | Ma | |
| 2007/0255570 A1 | 11/2007 | Annaz | |
| 2009/0138270 A1 | 5/2009 | Fletcher | |
| 2014/0220520 A1* | 8/2014 | Salamini | A61F 5/58 434/185 |
| 2014/0343945 A1* | 11/2014 | Benhaim | G06V 10/772 704/257 |
| 2015/0073803 A1* | 3/2015 | Boegelund | G10L 21/057 704/254 |
| 2015/0309700 A1 | 10/2015 | Li | |
| 2019/0114938 A1 | 4/2019 | Pergande | |
| 2019/0391640 A1 | 12/2019 | Prokofieva | |
| 2020/0034606 A1 | 1/2020 | Sipolins | |
| 2020/0126283 A1 | 4/2020 | Van Vuuren | |
| 2020/0126557 A1* | 4/2020 | Lee | G10L 15/22 |

FOREIGN PATENT DOCUMENTS

| | | |
|---|---|---|
| CN | 109150693 A | 1/2019 |
| CN | 110266645 A | 9/2019 |
| KR | 20100066866 A | 6/2010 |

OTHER PUBLICATIONS

Cao et al., "Expressive Speech-Driven Facial Animation," ACM Transactions on Graphics, Oct. 2005, 20 pages.

Li et al., "The Phoneme-Level Articulator Dynamics for Pronunciation Animation," 2011 International Conference on Asian Language Processing, Nov. 15-17, 2011, pp. 283-286.

Liu et al., "Geometry-guided Dense Perspective Network for Speech-Driven Facial Animation," IEEE Transactions on Visualization and Computer Graphics, arXiv:2008.10004v1 [cs.GR], Aug. 23, 2020, 12 pages.

Terissi et al., "A comprehensive system for facial animation of generic 3D head models driven by speech," EURASIP Journal on Audio, Speech, and Music Processing, Article No. 5 (2013), Feb. 1, 2013, 18 pages.

International Search Report and Written Opinion dated Apr. 22, 2022, for International Application No. PCT/CN2022/075990, filed Feb. 11, 2022.

* cited by examiner

GRAPHICAL ADJUSTMENT RECOMMENDATIONS FOR VOCALIZATION

BACKGROUND

Each language has specific audible qualities (e.g., phonemes) that are required for speech to match predetermined pronunciations. These audible qualities are often controlled by the shape that the mouth defines as the user is talking or vocalizing. For example, certain audible qualities require that the lips of the mouth define a specific shape, that the tongue defines a specific shape, that the tongue is in a specific configuration within the mouth (e.g., touching the top teeth, or elevated, or recessed), that the chin of the user is dropped to expand the space within the mouth, or the like. In some situations, a person can learn an "incorrect" pronunciation (e.g., a pronunciation that does not match a predetermined pronunciation as defined by a dictionary), such that this person needs to learn how to alter their physical manner of speaking in order to pronounce words "correctly."

SUMMARY

Aspects of the present disclosure relate to a method, system, and computer program product relating to providing graphical representations of suggested facial adjustments to a user, where these adjustments are determined to alter detected qualities of the vocalization of the user. For example, the method includes receiving audio data of a user voice as the user vocalizes during a period of time. The method also includes receiving spatial data of a face of the user during the period of time. The method also includes identifying, using the spatial data, positions of elements of the face relative to other elements of the face during the period of time, wherein relative positions of the elements cause a plurality of qualities of the user voice. The method also includes identifying that a subset of the positions of one or more of the elements cause a detected first quality of the plurality of qualities during the period of time. The method also includes determining alternate positions of the one or more elements that are determined to cause the user voice to have a second quality of the plurality of qualities rather than the first quality. The method also includes providing, to the user, a graphical representation of the face that depicts one or more adjustments from the subset of the positions to the alternate positions. A system and computer program product that are configured to execute operations of this method are also provided herein.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to providing recommendations to improve speech, while more particular aspects of the present disclosure relate to gathering spatial and audio data of a user while the user vocalizes and providing graphical representations of how the user can physically change how they vocalize in order to alter qualities of their vocalization. While the present disclosure is not necessarily limited to such applications, various aspects of the disclosure may be appreciated through a discussion of various examples using this context.

There are specific verbal qualities of the human voice that are desired in various settings. For example, to pronounce words within a given language correctly (e.g., where a correct pronunciation matches a predetermined pronunciation such as may be found in a dictionary), there may be specific qualities such as specific phonemes that a user has to make. For another example, to sing in a specific manner (e.g., in an operatic manner) there may be specific qualities such as timbres or tones that a user has to make. As used herein, a quality of a human vocalization is an audible characteristic that is dependent upon the shape that the oral cavity makes while the human is providing that quality (e.g., where that shape is made by the relative orientation of the jaws, mouth, lips, tongue, etc.). Though generally this disclosure speaks about a first quality (e.g., where this first quality is discussed herein as being either technically incorrect ala an incorrect dictionary definition and/or generally not preferred ala an "airy" singing voice) and a second quality (where this second quality is technically correct and/or generally preferred) for purposes of discussion, it is to be understood that aspects of this disclosure relate to detecting and addressing hundreds (or more) different types of qualities and/or severities of qualities as discussed herein.

As humans learn to speak in a language or sing or the like, they often do not initially have perfect pronunciation and perfect form as a result of not creating the correct set of physical movements with their face. For example, a person may have difficulty making one or more phonemes as a result of the person making an incorrect shape with their mouth. An example of this might include a person pronouncing the letter "L" incorrectly (e.g., similar to how a person should be pronouncing the letter "Y") as a result of the person failing to define a correct shape in which their tongue is touching the back of their upper incisors, a person being unable to pronouncing a "rolled r" (e.g., an alveolar trill, an alveolar flap, a retroflex trill, or a uvular trill), a person having difficulty pronouncing the diagraph <th> (e.g., such that the word "three" is instead pronounced as "tree"), or the like.

A person may attempt to fix this by using the services of a human specialist such as a speech pathologist, a voice coach, or the like. The specialist may be someone who has received highly specialized training in how to teach a person how to make specific shapes within their oral cavity in order to have preferred qualities of speech/song. This may be a frustrating and difficult process for some, as it can be hard to re-learn how to pronounce certain words (especially after a person has been pronouncing/vocalizing it in a certain way for a long period of time). Further, human specialists often have to resort to verbally describing how to define a new shape and/or show the new shape on themselves or on a doll/mannequin, as the human specialists are not able to physically cause another person to define that shape on their own. As such, in some examples it may be very difficult for a person who is speaking with a first quality to understand how they should change the physical way in which they speak in order to instead speak with a second quality.

Some conventional computing systems have attempted to streamline this situation by automating some of the process of detecting a user speaking with an "incorrect" quality. For example, conventional computing systems may calculate an amount of difference between a correct quality of speech and an incorrect quality of speech as spoken by a person. In some examples, conventional computing systems may further identify one or more aspects that are physically incorrect when it comes to the manner in which this person vocalizes. However, while these conventional computing systems may aid in correct diagnosis of speech problems, a person who is vocalizing with an incorrect/unpreferred quality may find these conventional computing systems unhelpful in learning how to instead vocalize with a correct/preferred quality.

Aspects of this disclosure may solve or otherwise address some or all of these problems. A computing device that includes a processing unit executing instructions stored on a memory may provide the functionality that addresses these problems, this computing device herein referred to as a controller. The controller may gather audio data and spatial data on a face and/or oral cavity of a user while the user is vocalizing. The controller may use this gathered data to identify the relative position(s) of elements on the face of the user while the user is vocalizing (e.g., speaking or singing), including tracking these positions across time as corresponding to different vocalizations. For example, the controller may generate a vector diagram of these elements that corresponds to the face of the user. The controller may determine whether or not there are any qualities of the voice of the user that do not meet certain thresholds. The controller may determine if any qualities do not meet certain thresholds by analyzing the audio data and/or by analyzing the spatial data. If any qualities do not meet these thresholds the controller may determine alternate positions of the elements that are determined to change the vocalizations from the unpreferred first quality to a preferred second quality. The controller may then graphically provide a representation of these alternate positions.

For example, the controller may provide an augmented image of the user that provides a graphical representation of these alternate positions. The controller may provide one or more augmented images of the user; for example, the controller may show one or more of a front view, a side view, and/or an internal view of the mouth of the user while the user vocalizes. The controller may use an augmented reality device to provide the graphical representation in real time over a current image of the face of the user. The augmented image of the user may highlight or indicate a few changes that a user should make in how to form/shape/move their mouth/tongue/face in order to change from the undesired first quality to the preferred second quality. In some examples, the controller may functionally provide this graphical representation in real-time (e.g., such that the position of elements of a user is detected and analyzed and responsive alternate positions are provided within milliseconds of a user making a face that defines these positions of elements), such that a user may receive immediate and dynamic visual tutelage regarding how to form/shape/move their mouth/tongue/face.

Further, though this discussion is largely discussed in terms of the controller suggesting facial adjustments in order to change from a first initial quality to a second and final quality, in some examples the controller may be suggesting the adjustment to achieve the second quality as a first step among a sequence of steps to perfect/preferred pronunciation. For example, the controller may determine that a dozen adjustments should be made for vocalization of the user to match perfect/preferred pronunciation. The controller may further identify that suggesting a dozen adjustments at once may be too confusing and/or difficult. As such, the controller may identify a series of adjustments for the user to make over time (e.g., from a first initial quality, to a second improved quality, to a third further improved quality, to a fourth final perfect quality), where each adjustment builds upon the preceding adjustment. The controller may provide these steps over time as a user masters each individual step. In some examples, such a progression may include specific "vector points" (e.g., where an element moves from an initial position to a predetermined intermediate position), such that after a user demonstrates that she can achieve an intermediate vector point the controller may further extend the vector points along a calculated vector that will eventually result in a preferred final vocalization quality as discussed herein.

Beyond this, aspects of this disclosure may be used to diagnose and/or provide therapy for conditions that relate to movement of the face. For example, aspects of this disclosure may detect a relative drooping of a smile on one side of a face for a given user over time (which may be indicative of a stroke). The disclosure may detect such medical conditions, and provide alerts to responsible parties in response to detecting them. Alternatively, and/or additionally, aspects of this disclosure may provide graphical representations of alternate positions that a user may create that reflect facial movements that are configured to improve facial mobility after a medical incident (e.g., after a stroke, or after a paralysis event, or the like). Similarly, where the controller determines that a user has both a medical condition that affects facial movement and also determines that the user has a speech with a quality that a user prefers to change, the controller may identify and provide those movements that the user is still able to execute (e.g., execute given the medical condition) that are able to change the first quality to a preferred second quality (e.g., even if this preferred second quality is not quite a perfect third quality).

Further, though this disclosure largely discusses how to improve a person speaking according to a predetermined perfect "dictionary" definition, one of ordinary skill in the art would understand that aspects of this disclosure also enable the controller to suggest facial adjustments that are configured to improve a singing voice of a user, have the controller assist the user in recreating a particular type of smile that the user likes (e.g., by telling the user to bring up one corner of a mouth, or having a user bring up their cheekbones, or "smile with their eyes," or the like), assist a person in creating a regional accent (e.g. if an actor is looking to perfect a Boston accent for a movie), or the like.

Figure 1:
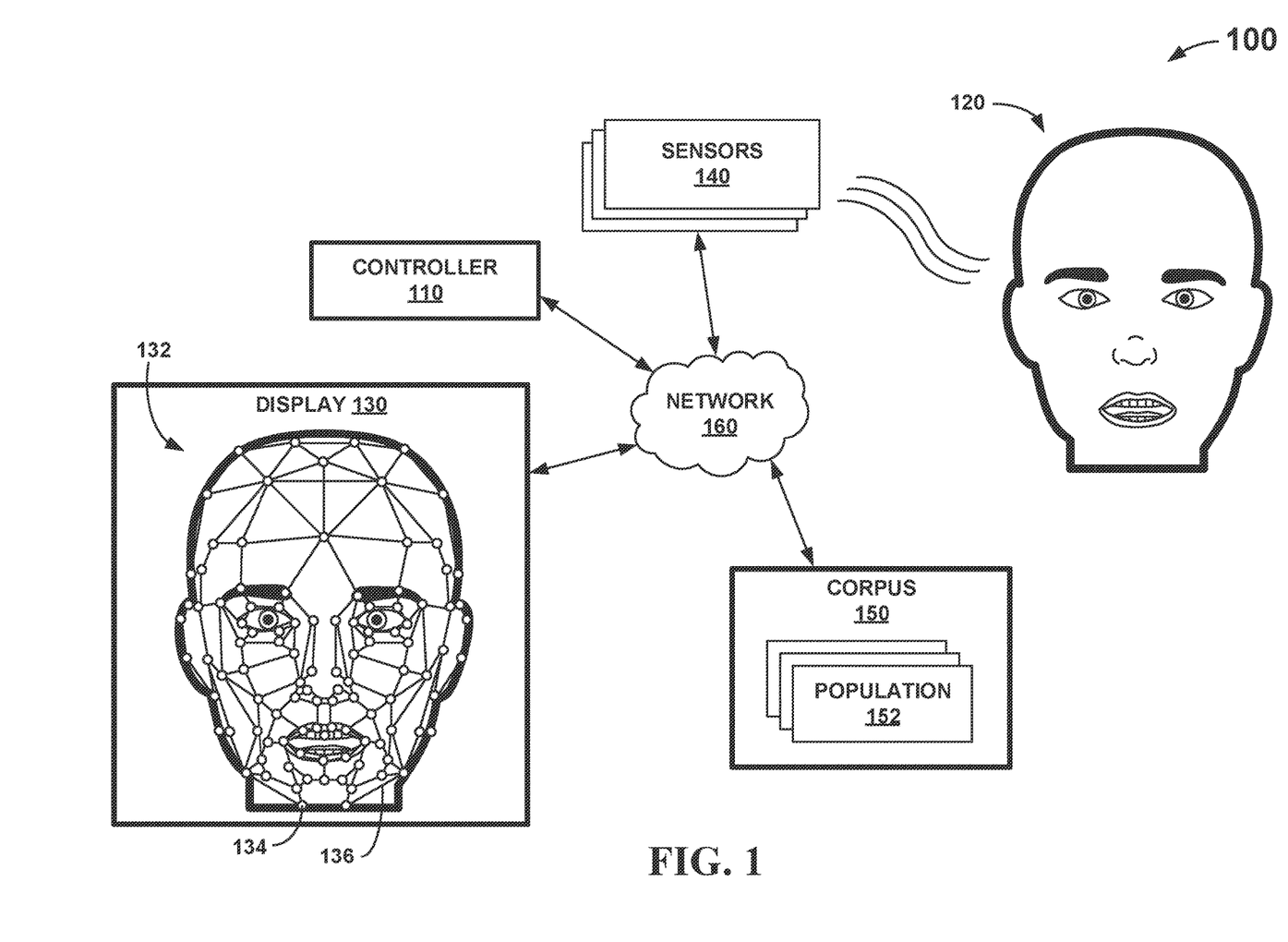
FIG. 1 depicts a conceptual diagram of an example system in which a controller may gather information on a user as the user is vocalizing so that the controller can then provide graphical representations of suggested facial adjustments to a user, where these adjustments are determined to alter detected qualities of the speech of the user.
Figure 3:
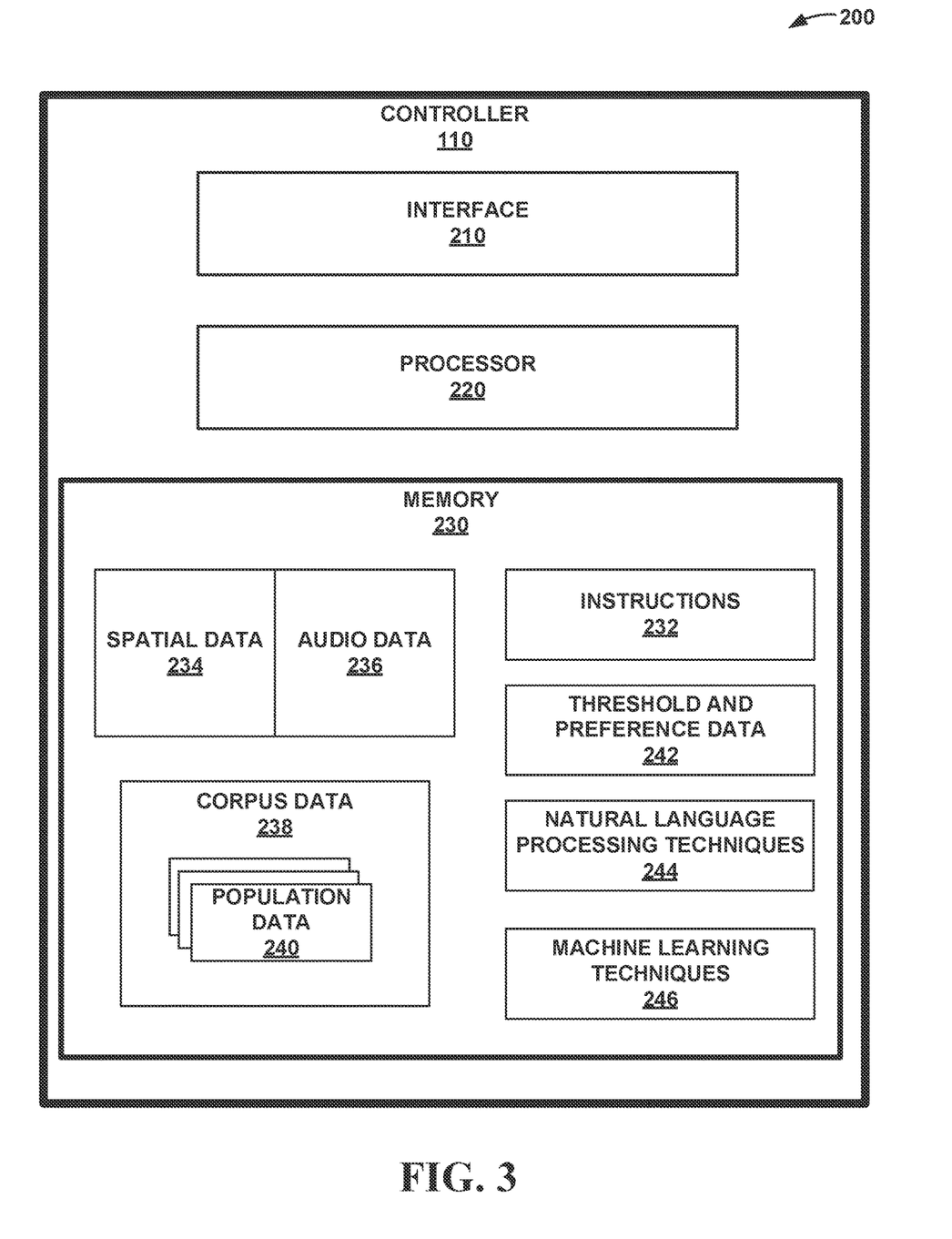
FIG. 3 depicts a conceptual box diagram of example components of the controller of FIG. 1.

For example, FIG. 1 depicts environment 100 in which controller 110 gathers audio and spatial data of user 120 as user 120 is verbalizing (e.g., speaking or singing or the like), and providing a graphical representation of determined adjustments. Controller 110 may include a processor coupled to a memory (as depicted in FIG. 3) that stores instructions that cause controller 110 to execute the operations discussed herein. Though controller 110 in FIG. 1 is depicted and discussed as a single component for purposes of discussion, in other examples controller 110 may include (or otherwise be a part of) numerous computing systems working together in some manner to execute the functionality described herein. Further, though controller 110 is generally discussed as providing the functionality herein as hosted within a computing device that is in a vicinity of user 120, it is to be understood that in other examples, some or all functionality of controller 110 can additionally and/or alternatively be virtualized such that the functionality can be aggregated from a plurality of distributed hardware components. When in such a distributed fashion, the functionality provided by controller 110 can be provided as a service in a cloud computing arrangement (e.g., via a web portal on a user device).

Controller 110 may provide the graphical representations of adjustments on display 130. Display 130 may be a computing device that is configured to graphically present images that are generated by controller 110. For example, display 130 may include a liquid crystal display (LCD), a light-emitting diode (LED) display, an organic light-emitting diode (OLED) display, or the like. In some examples, display 130 be a standalone device (e.g., a computer screen or a television), whereas in other examples display 130 may be integrated into a device that houses controller 110 or sensors 140 or the like (e.g., such that display 130 is part of a mobile phone).

Controller 110 may gather audio and/or spatial data of user 120 via sensors 140. Sensors 140 may include microphones that are precise enough to capture vocalizations of user 120, including identifying an ability to pronounce words in predetermined manners and/or an ability to sing with specific timbres. Sensors 140 may include cameras that are configured to capture many or all elements of a face of user 120 that cause a voice of user 120 to have one or more qualities. For example, elements may include different points along the lips, cheeks, jaws, or tongue of user 120, where different positions of these elements relative to the face of user 120 change a quality of a voice of user 120. An example of this might be a lowered jaw changing a quality of a voice, pursed lips changing a quality of a voice, raised cheekbones changing a quality of a voice, or the like. Controller 110 may identify position data related to each distinct facial feature (e.g., each lip, cheekbone, and jaw) using a plurality of elements. For example, controller 110 may use spatial data of a single lip of user 120 as gathered by a camera sensor 140 to determine five, ten, or more elements that are on that single lip, where if any of these elements deviated during vocalization that a quality of the vocalization would change.

In some examples, sensors 140 may include computing devices that are able to capture data on a position of a tongue of user 120 and/or a shape defined by an oral cavity of user 120. For example, sensors 140 may include a computing device that is configured to identify spatial data through the skin of user 120 from adjacent a face or cheek of user 120, such as an ultrasound device. For another example, sensor 140 may include a device that can go within the mouth of user 120, such as a mouthguard or a dental retainer. Such a mouthguard or retainer may be configured to be placed over the upper and/or lower teeth, and therein detect when the tongue touches the mouthguard/retainer (such that the tongue would be otherwise touching the upper or lower teeth, were it not for the mouthguard/retainer). In other examples, sensor 140 may include a tongue sleeve that can be worn over the tongue to detect when the tongue touches the teeth and/or detect a shape of the tongue. In certain examples, sensors 140 that can go within a mouth of user 120 may further be detected to measure distance between itself and other objects within the mouth (e.g., the outer bounds of the oral cavity as defined by the soft palate, the tongue, the uvula, etc.), with which controller 110 may determine a partial or full three-dimensional map of the oral cavity of user.

Controller 110 may analyze the spatial and/or audio data gathered by sensors 140 to compile a profile of user 120. This profile may include a spatial map of a face and/or mouth of user 120. For example, controller 110 may generate vector diagram 132 of user 120 as seen displayed on display 130. Vector diagram 132 may include a plurality of nodes 134 that are placed on each element of the face of user 120, where nodes 134 are connected via vectors 136. In some examples, controller 110 may create vector diagram 132 with a higher density of nodes 134 at regions that cause different qualities of speech (e.g., such that there are more nodes 134 near a mouth of user 120 than on a forehead of user 120). However, controller 110 may create nodes 134 at certain locations that do not relate to qualities of a voice of user 120 (e.g., such as ears of user 120) to better place vector diagram 132 on user 120 as user 120 naturally moves her head as she vocalizes (e.g., as the head of user 120 nods back and forth, shakes, or the like). It is to be understood that the specific number and arrangement of nodes 134 and vectors 136 within vector diagram 132 are provided purely for purposes of example only, and that more or less nodes 134 and vectors 136 provided in different locations for purposes consistent with this disclosure are considered.

In some examples, controller 110 may connect nodes 134 via vectors 136 when a movement of one node 134 will cause a movement of the respective connected node 134. Put differently, controller 110 may connect two nodes 134 when movement of the first node 134 inherently causes movement of the second node 134. In other examples, controller 110 may concentrate nodes 134 at locations that controller 110 determines that user 120 should focus on, so that the user can better detect granular adjustments that user 120 should make (and that further computational power is not used and/or "wasted" calculating and/or depicting nodes 134 and/or vectors 136 that are determined to be relatively less important to user 120).

Controller 110 analyzes the spatial and audio data of user 120 to identify whether or not user 120 is vocalizing with a first quality, where a first quality as discussed herein includes a quality that does not match a technical standard (e.g., a pronunciation guide within a dictionary) or a widely held preference (e.g., a rich and full timbre of a singing voice). Controller 110 may determine whether or not the vocalization is of such a first quality by comparing the vocalizations and/or spatial data during vocalizations of user 120 against corpus 150, where corpus 150 includes a large structured repository of data on a substantial amount of people vocalizing. Controller 110 may compare the vocalizations of user 120 against data of people within corpus 150 that are categorized within corpus 150 as vocalizing with a first quality (e.g., where words are not pronounced according to a dictionary definition, where a singing voice has a tone or timbre that is perceived as nasally or airy, etc.). Where controller 110 determines that an audible quality of user 120 matches a historical audio recording within corpus 150 (e.g., matches with a threshold amount of confidence) that is categorized within corpus 150 as reflecting such a first quality, controller 110 may determine that vocalizations of user 120 have a first quality.

Similarly, controller 110 may compare information on relative positions of elements of the face of user 120 during speech against relative facial positions of people as stored within corpus 150. For example, corpus 150 may be structured such that some stored historical relative facial positions during vocalization of certain words are categorized as causing vocalization of a first quality. Controller 110 may compare the relative positions of face elements as discussed herein against these categorized historical relative positions of corpus 150, such that if relative positions of elements of user 120 match a historical element position that is categorized as indicating a first quality, controller 110 may determine that vocalizations of user 120 are of a first quality.

In some examples, controller 110 may determine a severity of the first quality as exhibited by vocalizations of user 120. For example, some qualities of a vocalization may be non-binary, such that it may not be a manner of determining whether a phoneme is pronounced correctly or incorrectly, but rather whether a phoneme is pronounced correctly, slightly incorrectly, or dramatically incorrectly. An example of a speech impediment that is not necessarily binary but is frequently evaluated on a spectrum may include a lisp within the English language. Similarly, a singing voice may be identified on a spectrum where a first and relatively undesired quality is "airy" while a second and relatively desired quality is "rich," where there are many steps between an airy voice and a rich voice.

In examples where the first quality is quantifiable on a severity scale (e.g., a scale of 1-10) such that it is not binary, controller 110 may compare audio and spatial data of user 120 against sets of historical records of corpus 150 that are categorized (within corpus 150) as being different values on that severity scale, such that the respective set of historical records that match audio and/or spatial data indicate the severity of the first quality of vocalizations of user 120 (e.g., if a historical set of records that are a seven on the severity scale match the vocalization data of user 120, then controller 110 determines that the vocalization data of user has a first quality with a severity of seven).

Controller 110 determines alternate positions for elements of the face of user 120, where these alternate positions are determined to cause a voice of user 120 to change from a first quality to a second quality, where the second quality as discussed herein includes a quality that does match (or otherwise is a step in the direction of) a technical standard or a widely held preference. Controller 110 may determine the alternate positions by comparing the spatial data and/or the audio data of user 120 speaking to corpus 150, where corpus 150 includes spatial data and/or audio data of users 120 that are categorized as of that second quality.

In some examples, corpus 150 may include historical records of a single historical person speaking with both a first quality and also of a second quality (e.g., as the historical person learned how to speak with the second quality, potentially as a result of directed assistance from controller 110 as described herein). In such examples, where controller 110 determines that audio data and/or spatial data of user 120 matches historical data of a historical person that was categorized as vocalizing with a first quality, controller 110 may use spatial data of that same historical person vocalizing with the second quality to determine alternate positions for elements of the face of user 120. For example, controller 110 may determine relative changes of relative elements of the historical person as the historical person adjusted from vocalizing with the first to the second quality, and may apply changes that are scaled to match vector diagram 132 of user 120 to determine the alternate positions.

In some examples, controller 110 may analyze a plurality of relative historical changes within corpus 150 of a plurality of historical people within corpus 150 that have records of vocalizing with a first quality and a second quality, such that controller 110 may identify trends of, e.g., how different facial structures require different kinds of changes to change from the first quality to the second quality. Once controller 110 has analyzed corpus 150 to calculate these trends for various spatial arrangements, controller 110 may apply them to the respective vocalization data of user 120 to determine the adjustments.

Further, controller 110 may apply trends as determined by analyzing corpus 150 to account for a detected severity of a first quality of vocalizations of user 120. For example, where controller 110 detects that user 120 vocalizes with a first quality, controller 110 may determine a severity of the first quality where appropriate (e.g., where some mispronunciations or the like may be binary, and other mispronunciations or the like may be non-binary, as identified by controller 110). In such examples where controller 110 determines the severity, controller 110 may determine an adjustment that corresponds to this severity. For example, vocalizations with a first quality with a relatively low severity may require a relatively smaller adjustment to change vocalizations to a second quality, while vocalizations with a first quality with a relatively high severity may require relatively larger adjustments to change the vocalizations to a second quality.

Further, as discussed above, in some examples controller 110 may create a multi-step plan for changing vocalizations of user 120 from a first incorrect and/or unpreferred quality to a subsequent correct and/or preferred quality. For example, controller 110 may determine that too many adjustments are required for user 120 to reliably and accurately execute in a single adjustment. In such examples, controller 110 may break down the full set of adjustments into a series of adjustments that build upon each other, therein providing graphical representations of the first adjustment until user 120 masters in the first adjustment, after which providing the second adjustment until mastery is reached, etc. Controller 110 may learn over time how to break down full sets of adjustments in a manner that builds to correct and/or preferred vocalization qualities by evaluating how users 120 respond to provided adjustments (e.g., where some adjustments in some orders can cause regression, controller 110 is less likely to provide these adjustments in these orders in a subsequent session with a different user 120).

In some examples, controller 110 may identify one or more characteristics of user 120 that further define whether vocalizations are of a first quality or a second quality, and/or that generally categorize vector diagram 132 of user. For example, controller 110 may identify a language in which user 120 is vocalizing, a general face shape of user 120, an age of user 120, an accent of user 120, or the like. In such examples, controller 110 may then compare vocalizations of user 120 against a respective population 152 within corpus 150 that shares these characteristics to improve results at identifying that user 120 is speaking with a first quality and/or providing adjustments to user 120 to instead vocalize with the second quality. Controller 110 may identify over time which characteristics tend to cause users 120 to improve faster when controller 110 accounts for these characteristics, and therein organize populations 152 according to these characteristics. For example, controller 110 may determine that people past a certain age tend to have more wrinkles that changes how controller 110 can identify elements on a face of these people, such that controller 110 organizes populations according to people of a certain age (and/or with a threshold amount of wrinkles).

In some examples, controller 110 may receive a preferred characteristic of population 152 that user 120 wants to vocalize similar to. For example, as provided above, an actor may wish to acquire a regional dialect for an upcoming role, such that the actor selects population 152 of this region so that controller 110 may provide adjustments as necessary for the actor to perfect this dialect. Similarly, a regional reporter may want to drop their own regional dialect for a more neutral accent, and so may therein identify characteristics of a neutral accent for controller 110 to use.

In some examples, controller 110 may populate corpus 150. For example, controller 110 may autonomously populate corpus 150 with common linked words, phrases, letter pronunciations, or the like, so that controller 110 may search within corpus 150 for given words with given qualities. In other examples, a person who is trained at natural language processing (NLP) or the like may structure corpus 150 as described herein, potentially including creating one or more of populations 152. In certain examples, a person who is trained at NLP or the like may structure an initial corpus 150 that is big enough so that controller 110 may make determinations and/or calculations as discussed herein based on the data within corpus 150, upon which controller 110 may autonomously grow corpus 150 and grow populations 152 (including creating brand new populations 152) according to the existing structure and logic of corpus 150 and/or populations 152. Controller 110 may grow corpus 150 and/or populations 152 in this way in a supervised or unsupervised manner.

Controller 110 may interact with display 130, sensors 140, and/or corpus 150 over network 160. Network 160 may include a computing network over which computing messages may be sent and/or received. For example, network 160 may include the Internet, a local area network (LAN), a wide area network (WAN), a wireless network such as a wireless LAN (WLAN), or the like. Network 160 may comprise copper transmission cables, optical transmission fibers, wireless transmission, routers, firewalls, switches, gateway computers and/or edge servers. A network adapter card or network interface in each computing/processing device (e.g., controller 110, display 130, sensors 140, and/or corpus 150) may receive messages and/or instructions from and/or through network 160 and forward the messages and/or instructions for storage or execution or the like to a respective memory or processor of the respective computing/processing device. Though network 160 is depicted as a single entity in FIG. 1 for purposes of illustration, in other examples network 160 may include a plurality of private and/or public networks.

Figure 2A:
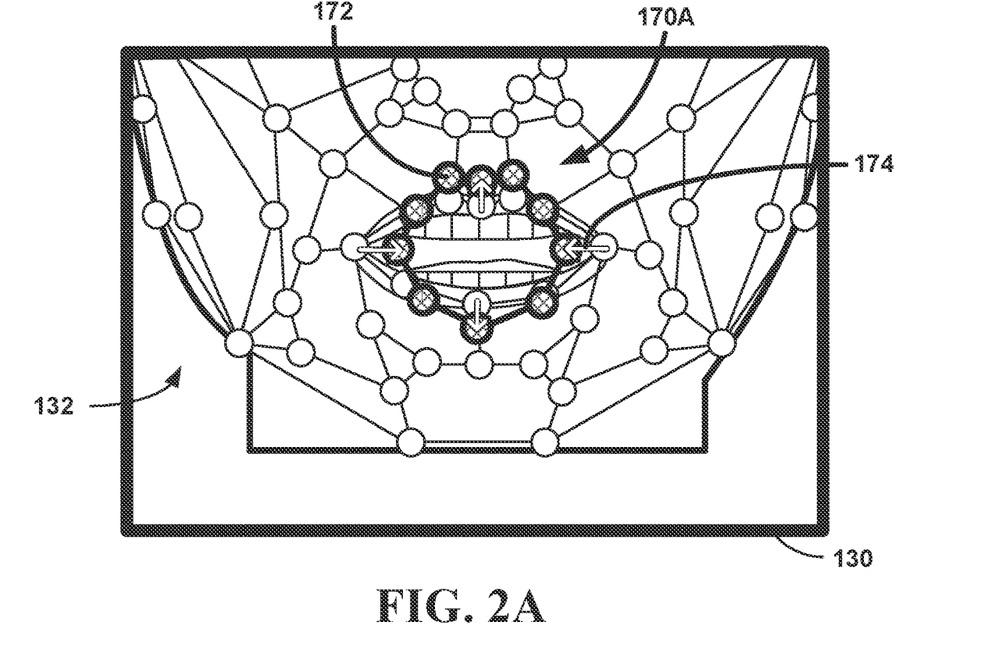
FIG. 2A depicts an example of an adjustment to a shape of the mouth of the user that the controller of FIG. 1 could graphically provide.
Figure 2B:
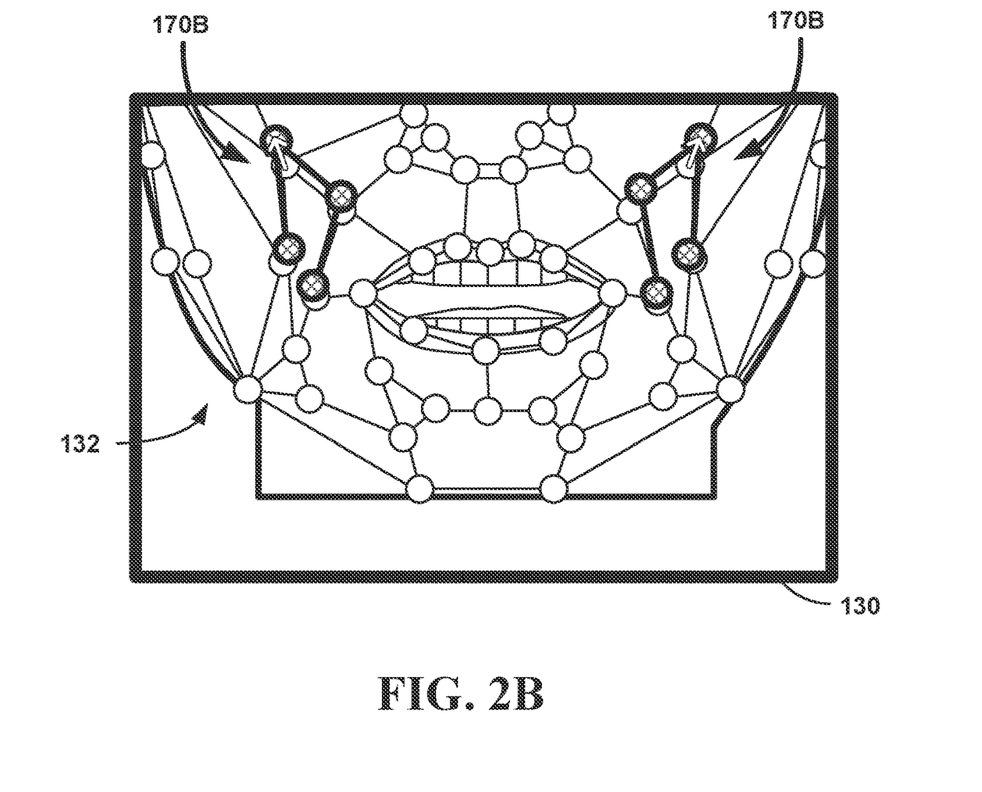
FIG. 2B depicts an example of an adjustment to a position of the cheekbones of the user that the controller of FIG. 1 could graphically provide.
Figure 2C:
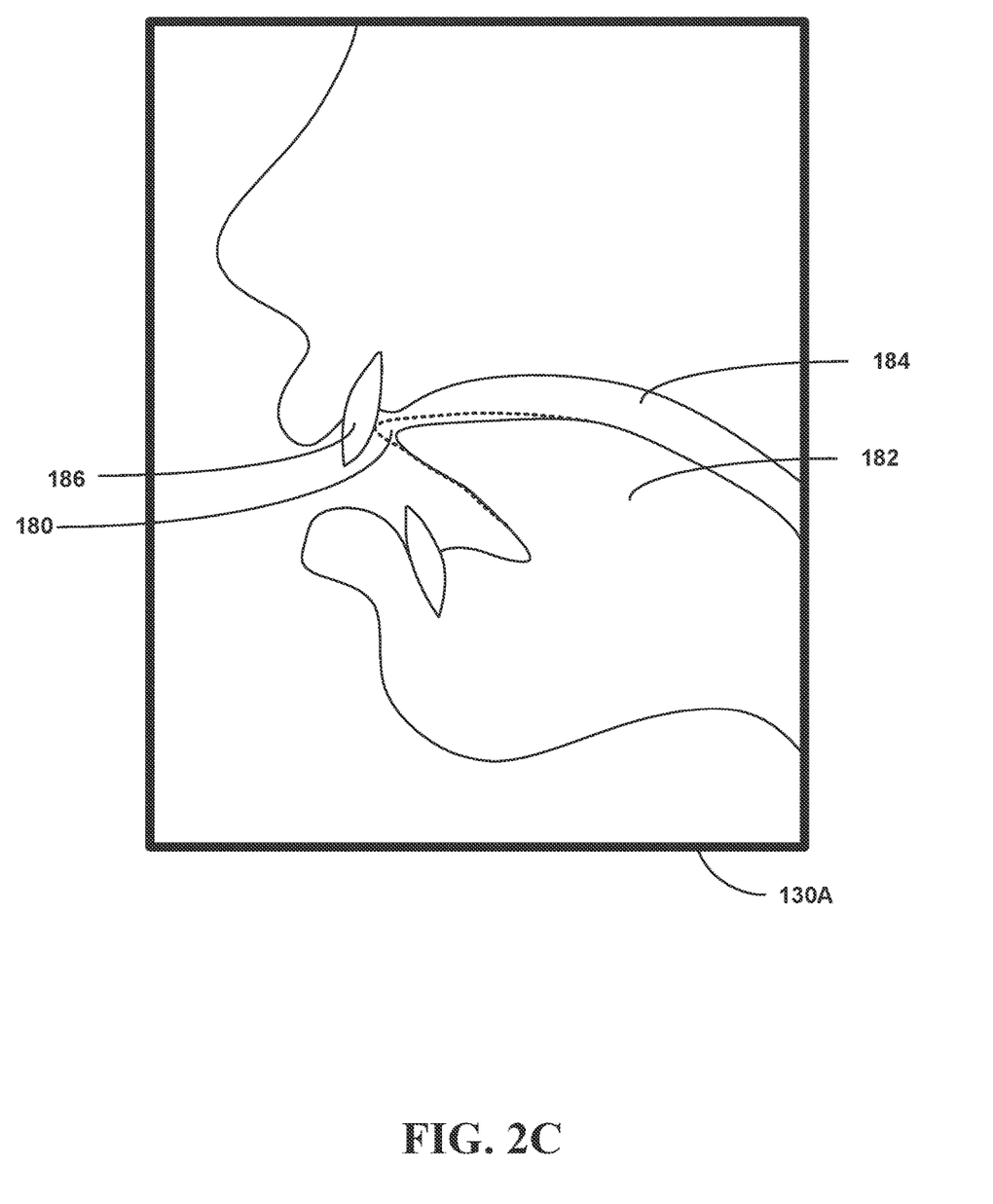
FIG. 2C depicts an example of an adjustment to a position of the tongue of the user that the controller of FIG. 1 could graphically provide.

FIGS. 2A-2C depict examples of graphical representations of a face of user 120 that depict adjustments from an initial position of elements that cause vocalizations in a first quality to a determined set of alternate positions that should cause vocalizations in a second quality. For example, FIG. 2A depicts an example adjusted vector diagram 170A with adjusted nodes 172 connected by adjusted vectors, where the adjusted nodes 172 indicate different positions for respective elements of a face of user 120. As depicted, adjusted vector diagram 170A has an adjustment in which user 120 puckers the mouth somewhat to form more of an "O" shape. Similarly, FIG. 2B depicts adjusted vector diagram 170B has an adjustment in which user 120 raises her cheekbones. In some examples, controller 110 may provide audible or text queues along with the graphical representations, such as audibly saying "make an O shape with your mouth," and/or providing text on display 130 which states "raise your cheekbones."

In some examples, controller 110 may further identify when any movement of user 120 as detected by sensors 140 that is an attempt to recreate adjusted vector diagrams 170A, 170B (collectively, adjusted vector diagrams 170) does not match adjusted vector diagrams 170. For example, controller 110 may inform user 120 if the user "overshoots" the suggested adjustments. Controller 110 may provide this feedback in a verbal form (e.g., by audibly stating "purse your lips just a bit less"), a textual form (e.g., by providing text on display 130 that states "lower your cheekbones a bit"), or in graphical form with updated adjusted vector diagrams 170 that show an adjustment back the "other" way.

As depicted, controller 110 may display adjusted vector diagrams 170 in addition to the initial vector diagram 132 on display. As depicted, adjusted vector diagrams 170 may be displayed differently than initial vector diagram 132. For example, adjusted vector diagrams 170 may be in different colors, bolded, highlighted, oversized, or the like as depicted in display 130.

As depicted, adjusted vector diagrams 170 may be graphically provided on display 130. Though display 130 shows only a lower half of the face of user 120 in both FIGS. 2A and 2B for purposes of illustration, it is to be understood that controller 110 may cause display to show more or less of the face of user 120 while controller 110 is providing a graphical representation of adjustments. As depicted, display may further depict graphical elements 174 that explicitly define the adjustments. For example, graphical elements 174 of FIG. 2A depict the outer edges of the mouth closing in. In some examples, controller 110 may only provide adjusted vector diagrams 170 and not graphical elements 174. In some examples, controller 110 may graphically demonstrate the adjustment from the initial vector diagram 132 to adjusted vector diagram 170 (e.g., such that nodes 172 of adjusted vector diagram 170 are graphically rendered as movable from their position according to adjusted vector diagram 170 to locations of the initial vector diagram 132 as moving along adjustments 174).

In some examples, controller 110 may provide a graphical representation of an interior of a mouth of a user, as depicted in FIG. 2C. Controller 110 may provide this graphical representation on display 130A, which may be substantially similar to display 130. In some examples, controller 110 may simultaneously provide a graphical representation of the interior of the mouth as depicted in FIG. 2C as well as the graphical representation of the face of user 120 as depicted in FIGS. 2A and/or 2B. In other examples, controller 110 may enable user 120 to switch between an interior view similar to FIG. 2C and the front view similar to FIGS. 2A and/or 2B.

As depicted, controller 110 may provide this graphical representation with adjustment 180. For example, as depicted in FIG. 2C, controller 110 may detect that tongue 182 within oral cavity 184 is not touching a top set of incisors 186 of user 120. Controller 110 may further detect that user 120 is attempting to say a letter "L," which is not possible to do according to a dictionary pronunciation when an element on the tip of tongue 182 defines the positional state depicted in FIG. 2C, such that user 120 instead speaks with a first quality (e.g., where the "L" sounds more like a "Y"). In response to this determination, controller 110 determines an adjustment 180 where an element on the top of tongue 182 touches the top incisors 186. As depicted, adjustment 180 of tongue 182 is depicted with dashed lines. In other examples, controller 110 may instead show adjustments with vector diagrams similar to FIGS. 2A and 2B (and in other examples, controller 110 may depict adjustments to a front face with dashed lines or the like rather than with adjusted vector diagrams 170).

As described above, controller 110 may include or be part of a computing device that includes a processor configured to execute instructions stored on a memory to execute the techniques described herein. For example, FIG. 3 is a conceptual box diagram of such computing system 200 of controller 110. While controller 110 is depicted as a single entity (e.g., within a single housing) for the purposes of illustration, in other examples, controller 110 may include two or more discrete physical systems (e.g., within two or more discrete housings). Controller 110 may include interface 210, processor 220, and memory 230. Controller 110 may include any number or amount of interface(s) 210, processor(s) 220, and/or memory(s) 230.

Controller 110 may include components that enable controller 110 to communicate with (e.g., send data to and receive and utilize data transmitted by) devices that are external to controller 110. For example, controller 110 may include interface 210 that is configured to enable controller 110 and components within controller 110 (e.g., such as processor 220) to communicate with entities external to controller 110. Specifically, interface 210 may be configured to enable components of controller 110 to communicate with display 130, sensors 140, corpus 150, or the like. Interface 210 may include one or more network interface cards, such as Ethernet cards and/or any other types of interface devices that can send and receive information. Any suitable number of interfaces may be used to perform the described functions according to particular needs.

As discussed herein, controller 110 may be configured to identify incorrect or otherwise unpreferred vocalizations of user 120 and graphically provide adjustments to a face of user 120 that would change the vocalizations. Controller 110 may utilize processor 220 to thusly provide facial adjustments to user 120. Processor 220 may include, for example, microprocessors, digital signal processors (DSPs), application specific integrated circuits (ASICs), field-programmable gate arrays (FPGAs), and/or equivalent discrete or integrated logic circuits. Two or more of processor 220 may be configured to work together to suggest facial adjustments accordingly.

Processor 220 may suggest facial adjustments to user 120 according to instructions 232 stored on memory 230 of controller 110. Memory 230 may include a computer-readable storage medium or computer-readable storage device.

In some examples, memory 230 may include one or more of a short-term memory or a long-term memory. Memory 230 may include, for example, random access memories (RAM), dynamic random-access memories (DRAM), static random-access memories (SRAM), magnetic hard discs, optical discs, floppy discs, flash memories, forms of electrically programmable memories (EPROM), electrically erasable and programmable memories (EEPROM), or the like. In some examples, processor 220 may suggest facial adjustments as described herein according to instructions 232 of one or more applications (e.g., software applications) stored in memory 230 of controller 110.

In addition to instructions 232, in some examples gathered or predetermined data or techniques or the like as used by processor 220 to suggest facial adjustments as described herein may be stored within memory 230. For example, memory 230 may include information described above that is gathered from user 120 during vocalization such as spatial data 234 and audio data 236. As depicted, spatial data 234 and audio data 236 may be stored within memory 230 as related, where each given set of spatial data 234 corresponds to a point in time at which audio data 236 is recorded. Further, in some examples memory 230 includes some or all of corpus data 238, including some or all respective population data 240 of corpus 150. In some examples, controller 110 may pull in local copies of records from corpus 150 that match characteristics of user 120, where these local copies are stored in memory 230 until an analysis of user 120 is complete.

Further, memory 230 may include threshold and preference data 242. Threshold and preference data 242 may include thresholds that define a manner in which controller 110 provides facial adjustments to user 120. For example, threshold and preference data 242 may provide preferred means for engagement, which may detail a manner in which user 120 prefers for adjustments to be displayed or suggested. Threshold and preference data 242 may also include a threshold deviation from a baseline that is required to cause controller 110 to suggest a facial adjustment. For example, a user may specify within threshold and preference data 242 that controller 110 is only to provide a facial suggestion for certain types of qualities, or for qualities of certain detected severities, or the like.

Memory 230 may further include natural language processing (NLP) techniques 244. Controller 110 may use NLP techniques to determine what user 120 is saying so that controller 110 may determine whether user 120 is saying it correctly and/or in a preferred manner. NLP techniques 244 can include, but are not limited to, semantic similarity, syntactic analysis, and ontological matching. For example, in some embodiments, processor 220 may be configured to gather natural language data as gathered during vocalization to determine semantic features (e.g., word meanings, repeated words, keywords, etc.) and/or syntactic features (e.g., word structure, location of semantic features in headings, title, etc.) of this natural language data in order to determine what words user 120 is saying (e.g., and compare this to similar words of corpus 150).

Memory 230 may further include machine learning techniques 246 that controller 110 may use to improve a process of suggesting facial adjustments to users as discussed herein over time. Machine learning techniques 246 can comprise algorithms or models that are generated by performing supervised, unsupervised, or semi-supervised training on a dataset, and subsequently applying the generated algorithm or model to suggest facial adjustments to user 120. Using these machine learning techniques 246, controller 110 may improve an ability of suggesting facial adjustments to user 120 over time. For example, controller 110 may identify over time certain characteristics of populations 152 that provide more relevant historical corollaries, which types of adjustments cause users 120 to change from vocalizing in a first quality to a second quality faster and/or more repeatedly, to improve a rate of identifying and calculating qualities and severities, and the like.

Specifically, controller 110 may learn how to provide facial adjustments under supervised machined learning techniques 246 from one or more human operators that edits "vectors" including "vector points" as controller 110 initially provides vector diagrams 132. For example, this may include human operators cancelling and/or repositioning nodes 134 as provided by controller 110, and/or cancelling and/or repositioning nodes 172 of adjusted vector diagrams 170. This may include teaching what controller 110 is to do in response to detecting that user 120 has moved their mouth/face/tongue in an attempt to replicate one of adjusted vector diagrams 170. This may include causing controller 110 to provide positive feedback (e.g., verbally and/or graphically congratulating user 120 on positively matching the graphical representation of the facial adjustment), provide negative feedback (e.g., verbally and/or graphically correct user 120 and explain one or more specifically ways in which user 120 didn't map to the graphical representation of the facial adjustment), detect that user 120 has mastered the current facial adjustment and instead provide a next step in a sequence of facial adjustments, and/or have user 120 repeat training of replicating this provided facial adjustment.

Further, one or more trained operators may train controller 110 using machine learning techniques 246 as described herein to track the face/mouth/tongue of user 120. For example, one or more trained operators may change how nodes 134 and/or vectors 136 are arranged on user 120 face over time. This may include providing feedback when nodes 134 and/or vectors 136 become untethered from the facial recognition location, in response to which controller 110 may remapping the facial recognition of user 120.

Machine learning techniques 246 can include, but are not limited to, decision tree learning, association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques. Specifically, machine learning techniques 244 can utilize one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBRT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), classification and regression tree (CART), chi-squared automatic interaction detection (CHAID), expectation-maximization algorithm, feedforward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning algorithms.

Figure 4:
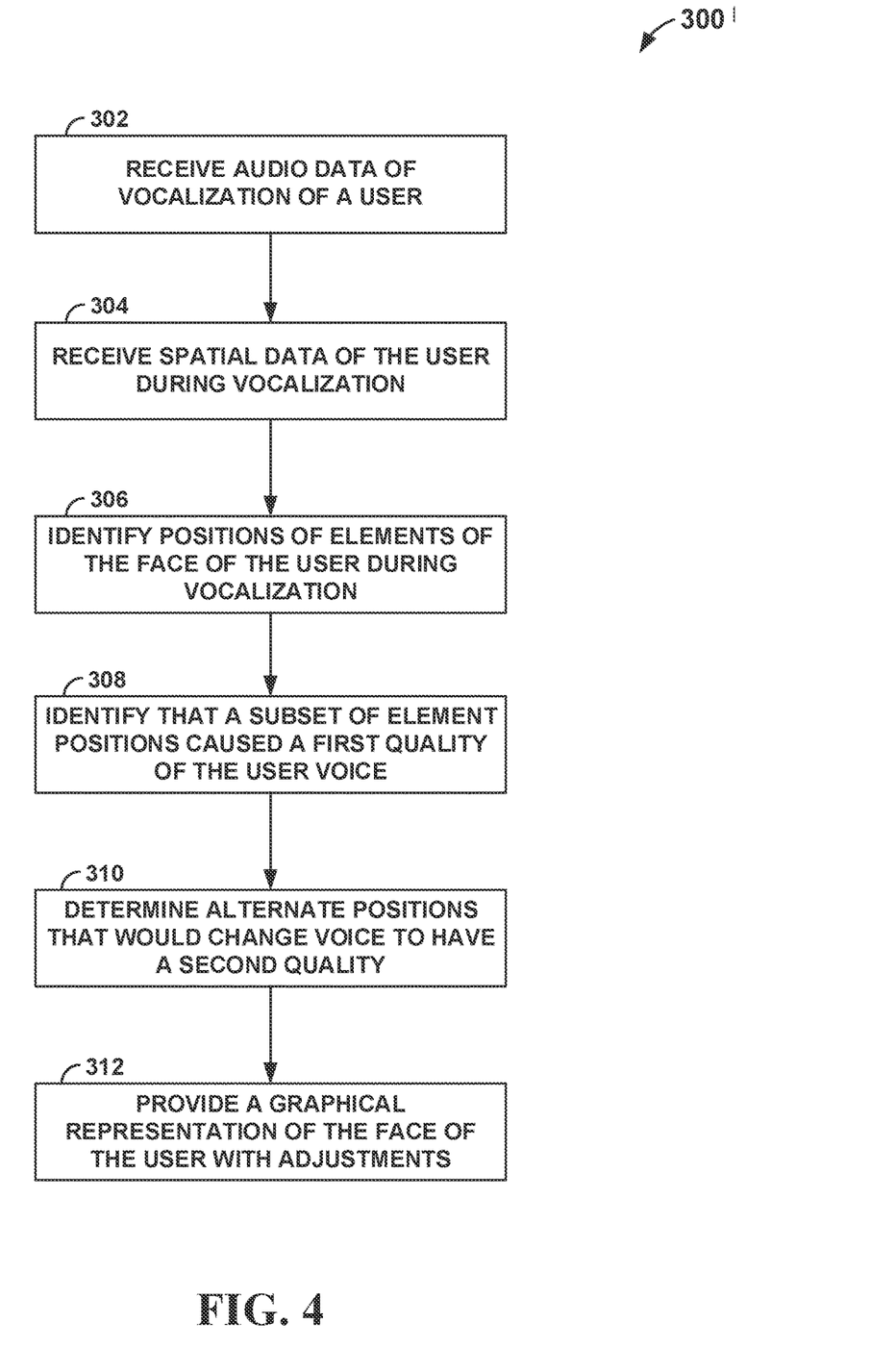
FIG. 4 depicts an example flowchart by which the controller of FIG. 1 may graphically provide face adjustments recommendations to alter qualities of the speech of the user.

Using these components, controller 110 may provide graphical representations of suggested facial adjustments to user 120 is response to detected vocalization qualities as discussed herein. For example, controller 110 may suggest facial adjustments according to flowchart 300 depicted in FIG. 4. Flowchart 300 of FIG. 4 is discussed with relation to FIG. 1 for purposes of illustration, though it is to be understood that other systems may be used to execute flowchart 300 of FIG. 4 in other examples. Further, in some examples controller 110 may execute a different method than flowchart 300 of FIG. 4, or controller 110 may execute a similar method with more or less steps in a different order, or the like.

Controller 110 receives audio data of user 120 vocalizing (302). This may include the user singing or speaking in one or more languages. Controller 110 additionally receives spatial data of user 120 during the vocalization (304). Controller 110 may receive both the vocalization audio data and the spatial data from a single sensor 140 (e.g., a single device that records both audio and video). In other examples, controller 110 receives vocalization audio data from a first (set of) sensor(s) 140 and spatial data from a second (set of) sensor(s) 140. Where controller 110 receives audio vocalization data separately from some or all spatial data, controller 110 may sync up all audio and spatial data.

Controller 110 identifies positions of elements of the face of user 120 during vocalization (306). As discussed herein, relative positions of these elements cause a plurality of qualities of the voice of user 120. In some examples, identifying the position of elements includes generating vector diagram 132 for the face of user 120 as described herein.

Controller 110 identifies a subset of the positions of one or more elements of the user face that cause the vocalization to be of a first quality (308). For example, controller 110 may compare the audio data and/or the spatial data against data of corpus 150 to identify that the vocalization was of the first quality, in response to which controller 110 determines which specific element positions cause the first quality.

Controller 110 determines alternate positions of these elements that would change vocalizations to have the second quality (310). Controller 110 may determine these alternate positions by identifying alternate positions of historical records of corpus 150 that cause similar people to vocalize with the second quality rather than the first quality. Once controller 110 determines these alternate positions, controller 110 provides a graphical representation of the face of user 120 with adjustments (312). The adjustments may detail how user 120 may move their face and/or tongue from the initial positions (in which user 120 vocalized with the first quality) to an alternate position (in which user 120 can vocalize with the second quality). For example, controller 110 may provide on display 130 adjusted vector diagrams 170 as described herein.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-situation data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising:
receiving audio data of a user voice as the user vocalizes during a period of time;
receiving spatial data of a face of the user during the period of time;
identifying, using the spatial data, positions of elements of the face relative to other elements of the face during the period of time, wherein relative positions of the elements cause a plurality of qualities of the user voice;
identifying that a subset of the positions of one or more of the elements cause a detected first quality of the plurality of qualities during the period of time;
determining alternate positions of the one or more of the elements that are determined to cause the user voice to have a second quality of the plurality of qualities rather than the first quality; and
providing, to the user, a graphical representation of the face that depicts the subset of the positions and the alternate positions and one or more adjustments therebetween, wherein the graphical representation is rendered to show movement from the subset positions to the alternate positions and the one or more adjustments therebetween.

2. The computer-implemented method of claim 1, wherein:
the identifying positions of elements includes identifying an initial vector diagram of the face of the user;
the determining alternate positions includes determining an adjusted vector diagram of the face of the user; and
the providing the graphical representation of the face includes providing both the initial vector diagram and the adjusted vector diagram.

3. The computer-implemented method of claim 1, wherein the graphical representation is provided in real time such that real-time position of the elements of the user is detected and analyzed and responsive alternate positions are provided within milliseconds of the user making a face that defines these real-time positions of elements.

4. The computer-implemented method of claim 3, further comprising using an augmented reality device to provide the graphical representation in real time over a current image of the face of the user.

5. The computer-implemented method of claim 1, further comprising gathering data on a position of a tongue of the user within a mouth of the user, wherein the positions of elements of the face includes elements on the tongue of the user and the one or more adjustments includes an alternate position of at least one element of the elements on the tongue.

6. The computer-implemented method of claim 5, wherein one of an ultrasound sensor, mouthguard, retainer, or tongue sleeve gathers the data on the position of the tongue.

7. The computer-implemented method of claim 1, further comprising:

identifying an age and a language of the user; and
identifying a machine learning model that has been trained specifically for the age and the language, wherein the machine learning model does each of:
the receiving the audio data;
the receiving the spatial data;
the identifying the positions of elements;
the identifying how the subset of the positions cause the first quality; and
the determining the alternate positions of the one or more of the elements.

8. The computer-implemented method of claim 1, further comprising identifying a face shape of the user by analyzing the spatial data, wherein the determining the alternate positions includes comparing the face against a corpus of faces with similar face shapes.

9. The computer-implemented method of claim 1, further comprising determining a severity of the first quality, wherein the adjustments account for the determined severity.

10. The computer-implemented method of claim 1, further comprising:
determining final positions of the one or more of the elements that are determined to cause the user voice to have an eventual final quality rather than the first quality;
determining that a difficulty of the user adjusting straight from the subset of positions to the final positions is higher than a threshold; and
determining a series of subsequent positions that progress a user from the first quality to the final quality in response to determining that the difficulty is higher than the threshold, wherein the series of subsequent positions includes the alternate positions as an intermediate position between the subset of positions and the final positions.

11. A system comprising:
a processor; and
a memory in communication with the processor, the memory containing instructions that, when executed by the processor, cause the processor to:
receive audio data of a user voice as the user vocalizes during a period of time;
receive spatial data of a face of the user during the period of time;
identify, using the spatial data, positions of elements of the face relative to other elements of the face during the period of time, wherein relative positions of the elements cause a plurality of qualities of the user voice;
identify that a subset of the positions of one or more of the elements cause a detected first quality of the plurality of qualities during the period of time;
determine alternate positions of the one or more of the elements that are determined to cause the user voice to have a second quality of the plurality of qualities rather than the first quality; and
provide, to the user, a graphical representation of the face that depicts the subset of the positions and the alternate positions and one or more adjustments therebetween, wherein the graphical representation is rendered to show movement from the subset positions to the alternate positions and the one or more adjustments therebetween.

12. The system of claim 11, wherein:
the identifying positions of elements includes identifying an initial vector diagram of the face of the user;

the determining alternate positions includes determining an adjusted vector diagram of the face of the user; and the providing the graphical representation of the face includes providing both the initial vector diagram and the adjusted vector diagram.

13. The system of claim 11, wherein the graphical representation is provided in real time such that real-time position of the elements of the user is detected and analyzed and responsive alternate positions are provided within milliseconds of the user making a face that defines these real-time positions of elements.

14. The system of claim 13, the memory containing further instructions that, when executed by the processor, cause the processor to use an augmented reality device to provide the graphical representation in real time over a current image of the face of the user.

15. The system of claim 11, the memory containing further instructions that, when executed by the processor, cause the processor to gather data on a position of a tongue of the user within a mouth of the user, wherein the positions of elements of the face includes elements on the tongue of the user and the one or more adjustments includes an alternate position of at least one element of the elements on the tongue.

16. The system of claim 15, wherein one of an ultrasound sensor, mouthguard, retainer, or tongue sleeve gathers the data on the position of the tongue.

17. A computer program product comprising one or more computer readable storage media, and program instructions collectively stored on the one or more computer readable storage media, the program instructions executable by one or more processors to cause the one or more processors to:

receive audio data of a user voice as the user vocalizes during a period of time;

receive spatial data of a face of the user during the period of time;

identify, using the spatial data, positions of elements of the face relative to other elements of the face during the period of time, wherein relative positions of the elements cause a plurality of qualities of the user voice;

identify that a subset of the positions of one or more of the elements cause a detected first quality of the plurality of qualities during the period of time;

determine alternate positions of the one or more of the elements that are determined to cause the user voice to have a second quality of the plurality of qualities rather than the first quality; and provide, to the user, a graphical representation of the face that simultaneously depicts the subset of the positions and the alternate positions and one or more adjustments therebetween, wherein the graphical representation is rendered to show movement from the subset positions to the alternate positions and the one or more adjustments therebetween.

18. The computer program product of claim 17, wherein:

the identifying positions of elements includes identifying an initial vector diagram of the face of the user;

the determining alternate positions includes determining an adjusted vector diagram of the face of the user; and the providing the graphical representation of the face includes providing both the initial vector diagram and the adjusted vector diagram.

19. The computer program product of claim 17, wherein the graphical representation is provided in real time such that real-time position of the elements of the user is detected and analyzed and responsive alternate positions are provided within milliseconds of the user making a face that defines these real-time positions of elements.

20. The computer program product of claim 19, the one or more computer readable storage media containing further instructions that, when executed by the one or more processors, cause the one or more processors to use an augmented reality device to provide the graphical representation in real time over a current image of the face of the user.

* * * * *